US00PP28687P2

(12) United States Plant Patent
Klinkhamer

(10) Patent No.: US PP28,687 P2
(45) Date of Patent: Nov. 21, 2017

(54) *HEUCHERA* PLANT NAMED 'PLUM POWER'

(50) Latin Name: ***Heuchera* hybrid**

Varietal Denomination: Plum Power

(71) Applicant: Lucas Klinkhamer, Hillegom (NL)

(72) Inventor: Lucas Klinkhamer, Hillegom (NL)

( * ) Notice: Subject to any disclaimer, the term of this patent is extended or adjusted under 35 U.S.C. 154(b) by 53 days.

(21) Appl. No.: 14/757,235

(22) Filed: Dec. 9, 2015

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

U.S. PATENT DOCUMENTS

PP21,857 P2 * 4/2011 Egger ..... Plt./440
PP24,771 P2 * 8/2014 Leue ..... Plt./440

OTHER PUBLICATIONS

New Plants and Flowers 2015 *Heuchera villosa* type with striking leaf markings, retrieved on Mar. 21, 2017, retrieved from the Internet at <http://www.newplantsandflowers.com/heuchera-villosa-type-with-striking-leaf-markings/> 2 pp.*

Upov Pluto Plant Variety Database 20170320 retrieved on Mar. 21, 2015, retrieved from the Internet at <http://www.upov.int/pluto/en/index.jsp> 1 page.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Plum Power', characterized by its unique foliage with leaves that are purple in color with a silver sheen, its large leaves, and its re-blooming habit; blooming from April to November in The Netherlands.

2 Drawing Sheets

Botanical classification: *Heuchera* hybrid.
Cultivar designation: 'Plum Power'.

BACKGROUND OF THE INVENTION

The present invention relates to a new and distinct cultivar of *Heuchera*, botanically of hybrid origin and known as a *Heuchera* 'Plum Power' and is hereinafter referred to by its cultivar name 'Plum Power'.

The new cultivar was discovered as a chance seedling by the Inventor in 2012 in his garden in Hillegom, The Netherlands. The parents of the new cultivar are unknown, however *Heuchera* 'Plum Pudding' (not patented) and *Heuchera* 'Regina' (not patented) are thought to be possible parents based on their proximity to the discovered seedling and the characteristics of the new cultivar.

Asexual propagation of the new cultivar was first accomplished by tissue culture using meristematic tissue under the direction of the Inventor in Rijswijk, Netherlands in May of 2015. Asexual propagation of the new cultivar by stem cuttings and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Plum Power' as a new and unique cultivar of *Heuchera*.

1. 'Plum Power' exhibits unique foliage with leaves that are purple in color with a silver sheen.
2. 'Plum Power' exhibits leaves that are very large in size.
3. 'Plum Power' exhibits a re-blooming habit; blooming from April to November in The Netherlands.

'Plum Power' can be most closely compared to its probable parents. 'Regina' is similar to 'Plum Power' in flower color. 'Regina' differs from 'Plum Power' in having more numerous flowering stems and in having leaves that are smaller in size. 'Plum Pudding' is similar to 'Plum Power' in having foliage that is similar in color. 'Plum Pudding' differs from 'Plum Power' in having less flowering stems, smaller leaves, and in having a more vigorous growth habit. 'Plum Power' can also be compared to 'Carnival Plum Crazy' (U.S. Plant Pat. No. 24,771) and 'Sugar Plum' (U.S. Plant Pat. No. 21,857). Both are similar to 'Plum Power' in having leaves with purple and silver coloration. 'Carnival Plum Crazy' differs from 'Plum Power' in having foliage that is less variable from spring to fall, in having a less vigorous growth habit, and in blooming only once in the season. 'Sugar Plum' is differs from 'Plum Power' in having smaller leaves with more silver throughout the season and in having shorter inflorescences.

BRIEF DESCRIPTION OF THE DRAWINGS

The accompanying colored photographs illustrate the overall appearance and distinct characteristics of the new

*Heuchera*. The photographs were taken of a plant two years in age as grown outdoors in a 25-cm container in Hillegom, The Netherlands.

Figure 1:
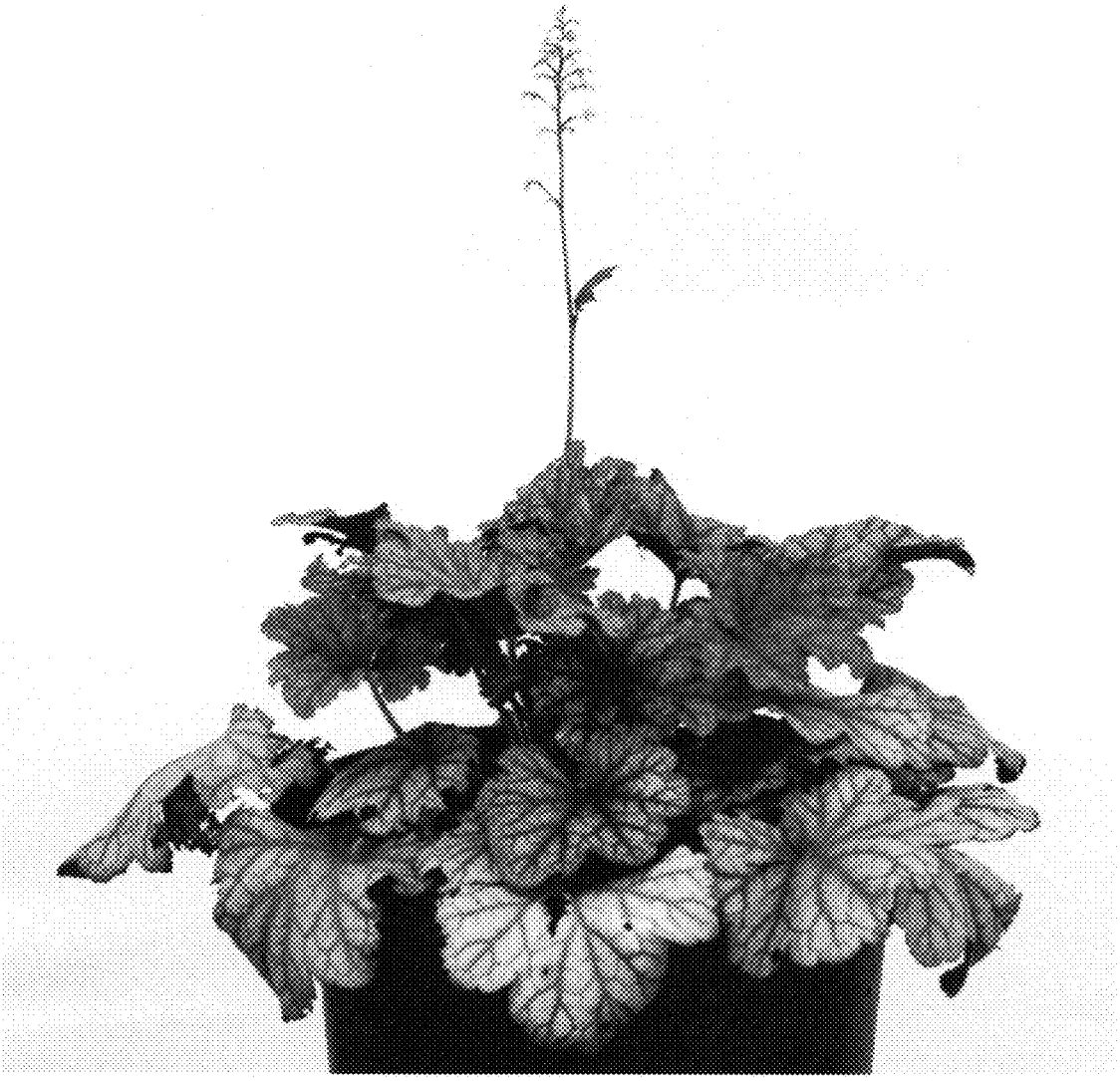

The photograph in FIG. 1 provides a side view of the plant habit and foliage coloration of 'Plum Power'.

Figure 2:
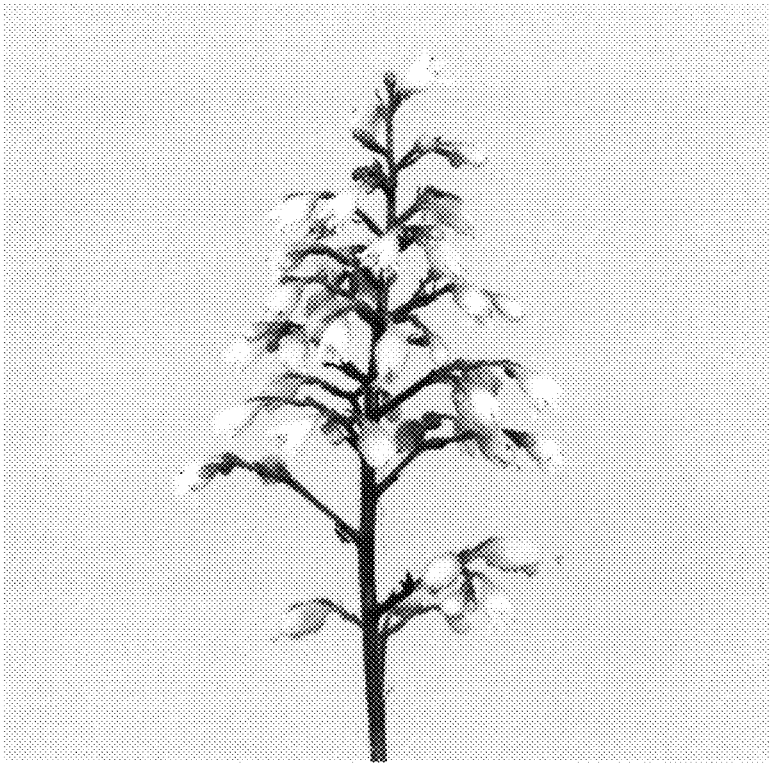

The photograph in FIG. 2 provides a close-up view of an inflorescence of 'Plum Power'.

Figure 3:
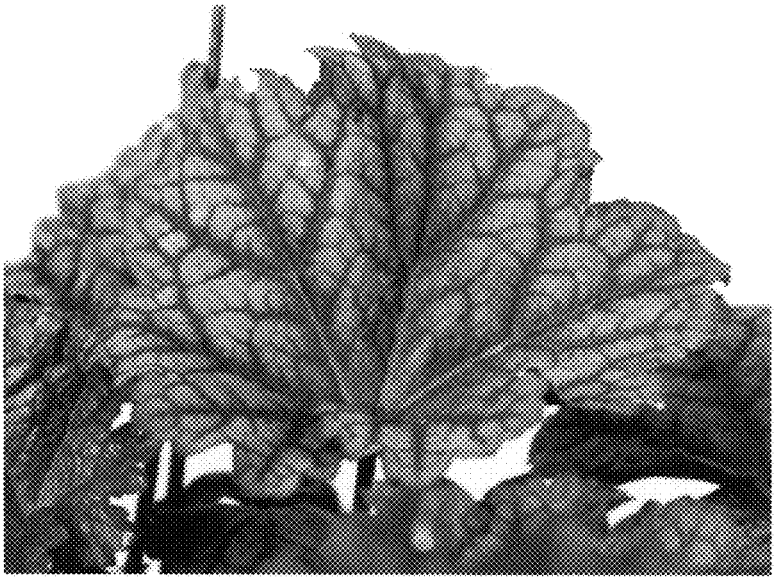

The photograph in FIG. 3 provides a close-up view of a leaf of 'Plum Power'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown outdoors in 25-cm containers in Hillegom, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Re-blooming from April to November in The Netherlands.

*Plant type*.—Herbaceous perennial.

*Plant habit*.—Clump-forming, mounded foliage.

*Height and spread*.—Average of 25 cm in height to top of foliage and 35 cm in height to top of inflorescences and an average of 42 cm in width.

*Hardiness*.—At least in U.S.D.A. Zone 3.

*Diseases and pests*.—Not more susceptible to pests and diseases than other *Heuchera* varieties.

*Root description*.—Fibrous roots on woody rootstalks.

*Branching habit*.—Basal rosette, no lateral branches.

*Basal branching*.—No lateral stems only basal rosettes.

*Propagation*.—In vitro propagation is the preferred method, stem cuttings are also possible.

*Root development*.—An average of 2 months for a tissue culture plantlet to fully root in a 72-cell liner.

*Growth rate*.—Vigorous.

Foliage description:

*Leaf shape*.—Broad ovate to near orbicular.

*Leaf division*.—Simple.

*Leaf base*.—Hastate, lobes touching to slightly overlapping.

*Leaf apex*.—Very short and abruptly acute.

*Leaf venation*.—Reticulate, 200B, slightly fading to 197A in color on upper surface, 186B in color on lower surface.

*Leaf margins*.—Lobed with an average of 7 lobes per leaf, lobe margins crenate with abrupt acute tips on every tooth, moderately undulated.

*Leaf attachment*.—Petiolate.

*Leaf arrangement*.—Alternate, basal rosettes.

*Leaf orientation*.—Typically nearly horizontal to slightly cupped under.

*Leaf surface*.—Upper surface matte, lower surface moderately glossy, both sides moderately covered with short hairs; upper surface hairs are 0.3 mm in length and too small to measure color, lower surface hairs are 0.5 mm in length and too small to measure color.

*Leaf color*.—Young upper surface; between 183C and 187A, young lower surface; 187B to 187C, mature upper surface; N77D, fading between 195A and 197B in fall, mature lower surface; 187B, fading to 187C in fall.

*Leaf size*.—Average of 12.2 cm in length and 11.4 cm in width.

*Leaf quantity*.—15 per basal rosette.

*Petioles*.—Round in shape, average of 13.5 cm in length and 3 mm in width, color; N187D, surface is densely covered with soft very short hairs an average of 0.3 mm in length and too small to measure color.

*Stipules*.—Small leafy stipules at the base of each leaf, laciniate apex, with an average of 1.5 cm in length and 5 mm in width, 71A in color, surfaces are densely covered with short strigose hairs; an average of 1.5 mm in length and 156D in color.

Flower description:

*Inflorescence type*.—Axillary compound spike.

*Inflorescence size*.—An average of 39.8 cm in height from base of peduncle to top, 9.6 cm in height from the lowest flower to the top and 4.3 cm in width.

*Inflorescence number*.—An average of 3 compound spikes per 25-cm container at one time, moderate flower density.

*Flower fragrance*.—None.

*Flower quantity*.—Average of 75 per inflorescence.

*Flower lastingness*.—Average of one week, self cleaning.

*Flower buds*.—Obovate in shape, an average of 3.5 mm in diameter and 2 mm in length, 185C to 185D, top 158B to 158C in color.

*Flower aspect*.—Outward to slightly drooping.

*Flower type*.—Single, campanulate.

*Flower size*.—About 6 mm in depth and 6 mm in diameter.

*Petals*.—Average of 5, rotate arrangement and implanted in the hypanthium at base, oblanceolate in shape, margin is entire, apex is narrowly acute, upper and lower surface is matte and glabrous, color when opening and fully upper and lower surface NN155D, about 2.5 mm in length and 0.4 mm in width.

*Calyx*.—Campanulate, sepals fused to hypanthium, 4 mm in length and diameter.

*Sepals*.—5, fused into hypanthium, elliptic in shape, about 4 mm in length and 1 mm in width, margin is entire fused into hypanthium, apex is broadly acute, fused base, upper surface is matte, lower surface is densely covered with very short glandular hairs an average of 0.2 mm in length and too small to measure color, color; immature and mature upper surface 69C to 69D, tip is 146D, immature lower surface 185C to 185D, tip is 158B to 158C, mature lower surface 69C to 69D, base 181D.

*Bracts*.—None observed.

*Peduncles*.—Moderate in strength, primary peduncle; average of 39 cm in length and 2 mm in diameter, moderate strength, held at a 70° angle (straight on top of flowering stem), color of both surfaces; 183A to 183B, secondary peduncles; average of 8 mm in length, 0.8 mm in diameter, held at a 50° (0°=straight upright) to primary peduncle, color of both surfaces;

183A to 183B, surface moderately covered with short strigose hairs an average of 0.5 mm in length and 156D in color.

*Pedicels*.—Moderate in strength, average of 2 mm in length and 0.5 mm in diameter, color 199D, pedicel of primary flower of each spikelet straight on top of secondary pedicel, pedicels of secondary and tertiary flowers of each spikelet in an average angle of 45° (0°=straight on top of secondary peduncle), surface pubescent.

Reproductive organs:

*Gynoecium*.—Pistil; 2, stigma; 2 mm in length, pointed in shape, 1.8 mm in length and NN155A in color, style; 1.8 mm in length, NN155A in color, ovaries; 157D in color.

*Androcoecium*.—Stamens; 5, anthers; triangular in shape, about 0.5 mm in length and 168C in color, filament 3 mm in length and NN155D in color, no pollen was observed.

*Seed/fruit*.—No fruit or seeds detected to date.

It is claimed:

1. A new and distinct cultivar of hybrid *Heuchera* plant named 'Plum Power' as herein illustrated and described.

* * * * *